US009666974B2

(12) United States Patent
Bopp

(10) Patent No.: US 9,666,974 B2
(45) Date of Patent: May 30, 2017

(54) SOCKET INSERT FOR AN ELECTROSURGICAL DEVICE, ELECTROSURGICAL DEVICE WITH A SOCKET INSERT AND SET WITH A REMOVAL TOOL

(71) Applicant: ERBE Elektromedizin GmbH, Tuebingen (DE)

(72) Inventor: Benjamin Bopp, Ofterdingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 84 days.

(21) Appl. No.: 14/616,873

(22) Filed: Feb. 9, 2015

(65) Prior Publication Data

US 2015/0229083 A1 Aug. 13, 2015

(30) Foreign Application Priority Data

Feb. 10, 2014 (EP) .................................... 14154490

(51) Int. Cl.
*H01R 31/06* (2006.01)
*H01R 13/629* (2006.01)
(Continued)

(52) U.S. Cl.
CPC ......... *H01R 13/518* (2013.01); *H01R 13/743* (2013.01); *A61B 18/1206* (2013.01);
(Continued)

(58) Field of Classification Search
CPC ..... H01R 13/627; H01R 31/06; H01R 31/633
See application file for complete search history.

(56) References Cited

U.S. PATENT DOCUMENTS 6,200,160 B1 * 3/2001 Drexler ................ G02B 6/3897 439/536
6,361,242 B1 3/2002 Daoud
(Continued)

FOREIGN PATENT DOCUMENTS

CN 102665585 A 9/2012
DE 202011050061 U1 7/2011
(Continued)

OTHER PUBLICATIONS

Office Action in corresponding Korean Application No. 10-2015-0018753, dated Jun. 20, 2016, 9 pages.
(Continued)

*Primary Examiner* — Briggitte R Hammond
(74) *Attorney, Agent, or Firm* — Fitch, Even, Tabin & Flannery LLP

(57) ABSTRACT

The invention relates to a socket insert for an electrosurgical device with a front plate (10) comprising at least one plug opening (11), first and second side walls (12, 13) which are connected to the front plate (10) and bound a receiving space (14) for electronic components, and at least one latching device (15), which is connected to the first side wall (12) and can be transferred from a locked position into an unlocked position. At least the first side wall (12) includes a guide channel (16), which forms an access hole (17) in the front plate (10) and through which the latching device (15) can be manipulated for unlocking. The invention also relates to an electrosurgical device with a socket insert and a set with a removal tool.

16 Claims, 6 Drawing Sheets

100,140
13
14
135
10
28
18
15,30
27
18
16,17
12
11
120
110
17
18

(51) Int. Cl.

| | |
|---|---|
| ***H01R 13/518*** | (2006.01) |
| ***H01R 13/74*** | (2006.01) |
| *H01R 13/717* | (2006.01) |
| *A61B 18/12* | (2006.01) |
| *A61B 18/00* | (2006.01) |
| *H01R 13/633* | (2006.01) |
| *H01R 43/22* | (2006.01) |
| *A61B 18/14* | (2006.01) |

(52) U.S. Cl.
CPC ..... *A61B 18/14* (2013.01); *A61B 2018/00178* (2013.01); *H01R 13/633* (2013.01); *H01R 13/7172* (2013.01); *H01R 43/22* (2013.01); *H01R 2201/12* (2013.01); *Y10T 29/49117* (2015.01)

(56) References Cited

U.S. PATENT DOCUMENTS

| | | | | |
|---|---|---|---|---|
| 6,361,357 | B1 | 3/2002 | Stillwell et al. | |
| 6,435,727 | B1 * | 8/2002 | Fingler | G02B 6/3897 439/536 |
| 9,059,524 | B2 * | 6/2015 | Munkelt | H01R 13/15 |
| 2004/0097117 | A1 | 5/2004 | Gonnering | |
| 2004/0097912 | A1 | 5/2004 | Gonnering | |
| 2006/0223359 | A1 | 10/2006 | O'Connell et al. | |
| 2007/0032789 | A1 | 2/2007 | Gonnering et al. | |
| 2009/0269962 | A1 | 10/2009 | Miller et al. | |
| 2011/0087212 | A1 | 4/2011 | Aldridge et al. | |
| 2013/0267106 | A1 * | 10/2013 | Jenks | G11B 17/00 439/160 |
| 2014/0318199 | A1 * | 10/2014 | Gokcebay | E05C 3/042 70/278.1 |

FOREIGN PATENT DOCUMENTS

| | | | |
|---|---|---|---|
| EA | 007705 | B1 | 12/2006 |
| JP | H0684564 | A | 3/1994 |
| JP | 2002119517 | A | 4/2002 |
| JP | 2006506175 | A | 2/2006 |
| JP | 2007521049 | A | 8/2007 |
| WO | 2009018668 | A1 | 2/2009 |
| WO | 2011006821 | A1 | 1/2011 |

OTHER PUBLICATIONS

Office action and search report in corresponding Chinese application No. 201510061948.2, dated Sep. 5, 2016, 11 pages.
European Search Report of corresponding European patent application No. 14 15 4490, dated Aug. 11, 2014, 9 pages.
Office communication in corresponding European application No. 14 154 490.8, dated Mar. 3, 2016, 12 pages.
Japanese office action in corresponding Japanese application No. 2015-021934, dated May 31, 2016, 8 pages.
Japanese search report in corresponding Japanese application No. 2015-021934, dated Apr. 22, 2016, 14 pages.
Russian office action in corresponding Russian application No. 2015 104 125 dated Apr. 14, 2016, 8 pages.
Office Action in corresponding Russian Application No. 2015 104 125, dated Nov. 17, 2016, 9 pages.

* cited by examiner

SOCKET INSERT FOR AN ELECTROSURGICAL DEVICE, ELECTROSURGICAL DEVICE WITH A SOCKET INSERT AND SET WITH A REMOVAL TOOL

RELATED APPLICATION(S)

This application claims the benefit of European Patent Application No. EP 14154490.8 filed Feb. 10, 2014, the contents of which are incorporated herein by reference as if fully rewritten herein.

TECHNICAL FIELD

The invention relates to a socket insert for an electrosurgical device, an electrosurgical device with a socket insert of this kind and a set with a socket insert of this kind and a removal tool. The invention also relates to a method for removing such a socket insert.

BACKGROUND

Known from practice are electrosurgical devices, for example HF surgical devices, comprising a plurality of sockets for the connection of surgical instruments. The sockets form a plug-and-socket connection between the electrosurgical instruments and the switching circuits inside the electrosurgical device. The sockets are usually integrated in socket inserts which are secured in the electrosurgical device, preferably on the housing thereof.

During daily usage, it becomes necessary to replace a socket insert. For example, a user may wish to connect an electrosurgical instrument with a plug to a device, wherein the plug does not fit in the socket provided. This then requires the replacement of the socket insert. In addition, the plug-and-socket connections formed by the sockets are frequently manipulated resulting in a high degree of wear on the sockets. Consequently, it may be necessary to replace the sockets or socket inserts in order to ensure a secure plug-and-socket connection. Since the sockets in surgical devices known to date are securely anchored in the device, it is necessary to open the device to replace the sockets. Due to statutory provisions, an intervention of this kind on the device may only be performed by trained service engineers. It is also necessary to perform an extensive safety check when the device's housing has been reclosed. Safety checks of this kind are time-consuming and cost-intensive.

SUMMARY

The object of the invention consists in the disclosure of a socket insert for an electrosurgical device that enables simple replacement, wherein the replacement can be performed without a subsequent safety check. The object of the invention also consists in the disclosure of an electrosurgical device with such a socket insert and a set with such a socket insert and a removal tool. A further object of the invention consists in the disclosure of a method for removing such a socket insert.

For example, a socket insert for an electrosurgical device with a front plate including at least one plug opening. The socket insert also comprises first and second side walls, which are connected to the front plate and bound a receiving space for electronic components. The socket insert also comprises at least one latching means, which is connected to the first side wall and may be transferred from a locked position into an unlocked position. At least the first side wall comprises a guide channel, which forms an access hole in the front plate and through which the latching means can be manipulated for unlocking.

A socket insert is arranged such that the removal of the socket insert is possible without having to open the housing of the electrosurgical device. For example, the socket insert can be replaced while simultaneously avoiding manipulation in the interior of the electrosurgical device. To this end, the guide channel is provided which forms an access hole in the front plate. In this way, the guide channel enables access to a latching means used to unlock the socket insert. In particular, a guide channel for a manipulating element can at least be embodied in the first side wall, wherein the latching means can be manipulated by the manipulating element for unlocking. Therefore, the guide channel enables the manipulating means to access the latching means. Since the guide channel forms an access hole in the front plate the latching mechanism concealed in the interior of the socket insert is easily accessed from the outside. This facilitates the removal of the socket insert and avoids laborious disassembly of the electrosurgical device.

In a preferred embodiment of the socket insert according to the invention, an axially displaceable manipulating rod is arranged in the guide channel. Here, a first end of the manipulating rod can be embodied to unlock the latching means. Preferably, in particular for unlocking the latching means, the first end of the manipulating rod is arranged movably in the longitudinal direction of the guide channel. On the manipulation of the latching means, the first end of the manipulating rod leaves the guide channel in the direction of the interior space of the device. Hence, the manipulating means is arranged such that it can be moved out of the guide channel. It is generally provided that a manipulating means is guided in an axially displaceable way in the guide channel in order to manipulate the latching mechanism, i.e. the latching means is transferred into unlocked position. The manipulating means can, for example, be a tool with a correspondingly long unlocking rod, which completely penetrates the guide channel and in this way extends from the front plate as far as the latching means. It is particularly preferable for a manipulating rod to be arranged in the guide channel. The manipulating rod can comprise a first end, which acts on the latching means, and a second end, which, in locked position, is flush with the access hole in the front plate. This ensures that the guide channel is permanently sealed, which is advantageous for reasons of hygiene and aesthetics.

The length of the manipulating rod can be greater than the length of the guide channel. Preferably, the latching means is arranged in alignment with the guide channel on the first side wall. The latching means can be arranged directly on a rear outlet opening of the guide channel or at a distance thereto. The position of the latching means arranged at distance to the rear outlet opening of the guide channel influences the loading of the latching means, which is preferably made of plastic. If the first end of the manipulating rod lies directly on the latching means, the path length for the manipulation of the latching means is reduced. This means only a short stroke is necessary for the manipulation of the latching means.

The manipulating rod or the first end of the manipulating rod can moreover comprise a stop, which interacts with the guide channel to limit the axial movement of the manipulating rod. The stop can, in particular, interact with the rear outlet opening of the guide channel. The stop on the manipulating rod ensures that the manipulating rod remains in the socket insert. Insofar, the stop forms a loss prevention device.

In a further preferred embodiment of the present invention, the latching means comprises a wedge-shaped projection, which is in alignment with the manipulating rod and the height of which increases in the direction of advance of the manipulating rod. In other words, the projection comprises an inclination that increases as the distance to the rear outlet opening of the guide channel increases. This ensures that, by means of the axial advance of the manipulating rod, the latching means is simply transferred to the unlocked position. Consequently, this ensures simple and secure mechanical unlocking of the socket insert.

The latching means can also comprise an outwardly directed latching nose, which can be moved inward in the direction of the receiving space for unlocking. The unlocking direction inward toward the receiving space is advantageous with respect to the overall system since in this way a corresponding socket holder for the socket insert can be designed in structurally simple way. Overall, this enables a compact structure of both the socket insert and the overall system, in particular of the surgical device. This also prevents the latching mechanism from impeding a light path of an optional light guide surrounding the socket insert.

In a further preferred embodiment of the socket insert according to the invention, the first side wall and the second side wall each comprise a guide channel. Therefore, it is possible for two guide channels to be provided overall, wherein in each side wall of the socket insert a guide channel is arranged in each case. The guide channels can be arranged in parallel to each other. In particular, the guide channels can be arranged at the same height. If a guide channel is arranged in each side wall, wedging of the socket insert on removal from electrosurgical device, in particular of a socket holder of an electrosurgical device, is avoided. This increases the operating safety of the socket insert according to the invention.

With the socket insert according to the invention, in a preferred embodiment, the front plate can comprise a translucent frame, in particular a scattering frame. The frame or scattering frame can be connected to a light guide. It is also possible for the frame and the light guide to be formed from one part, as one piece and/or seamless. Generally, the socket insert can comprise a scattering frame surrounding the front plate. The translucent frame serves as an optical display for the operating mode of the electrosurgical device. The fact that this operating mode display is integrated in the socket insert improves the optical appearance of the entire electrosurgical device.

The light guide can in particular form a slide-in housing which completely surrounds the receiving space and can be connected to a light source. Insofar, the socket insert has a modular structure, wherein the individual modules can, for example, be formed by the receiving space bounded by the side walls and the front plate, the manipulating rod and the light guide. Generally, the modular structure of the socket insert facilitates its assembly.

In a further preferred embodiment of the invention, the slide-in housing comprises at least one complementary means for connection to the latching means of the side wall. The complementary means can be arranged on the inner wall of the slide-in housing outside the light path. The complementary means is used to fix the socket insert in the slide-in housing. Here, the latching means latches with the complementary means so that the socket insert is fixed in the slide-in housing. The arrangement of the complementary means is selected such that the complementary means does not impair the light path inside the slide-in housing. This ensures that the homogeneous light effect achieved by the slide-in housing is not disrupted by the latching means.

The present application discloses and claims an electrosurgical device with an above-described socket insert as an independent aspect. With the electrosurgical device, it is, for example, possible for the slide-in housing of the socket insert to be securely connected to the housing of the electrosurgical device. The socket insert or the receiving space bounded by the front plate and the side walls can have a latched connection to the housing of the electrosurgical device via the slide-in housing.

A further independent aspect of the invention relates to a set with at least one above-described socket insert and a removal tool. The removal tool can comprise at least one unlocking rod with a free end. The removal tool can also comprise two unlocking rods connected in a clip-like manner each having a free end. In any case, it is provided that the free end can be introduced into the guide channel. Here, to unlock the latching means, the free end can be guided completely through the guide channel and directly act on the latching means. Alternatively, the free end can interact with the manipulating rod, which is mounted in an axially displaceable way inside the guide channel. The manipulation of the latching means is then performed via the manipulating rod, which is displaced by the unlocking tool in the guide channel.

The unlocking rod can comprise a protruding edge at the free end. Preferably, the diameter of the free edge is smaller than the diameter of the guide channel. This facilitates the introduction of the unlocking rod into the guide channel.

The guide channel can comprise a recess which can be gripped from behind by the protruding edge to remove the socket insert from the device. In this way, the removal tool can be locked in the guide channel. Thus, the removal tool fulfils a dual function. On the one hand, the removal tool enables the displacement of the manipulating rod or direct manipulation of the latching means. On the other hand, the removal tool effects the removal of the socket insert since the removal tool can be at least temporarily be connected in a positive way to the guide channel in the side wall of the socket insert. In connected state, therefore, the removal tool forms a retaining clip on which the socket insert can be pulled out of the slide-in housing.

According to a supplementary independent aspect, the present application discloses a method for removing above-described socket insert from an electrosurgical device with which the removal tool is inserted into the guide channel of the socket insert with the unlocking rod and the socket insert is unlocked. In addition, with the method according to the invention, the removal tool is tilted and connected to the guide channel. The socket insert is removed from the device with the removal tool, in particular drawn out. Hence, the invention discloses a comparatively simple method for removing a socket insert from an electrosurgical device that avoids the need to open the device. The method according to the invention can therefore also be carried out by untrained staff and avoids or saves a subsequent safety check.

The invention will described in more detail in the following with reference to exemplary embodiments and the enclosed schematic drawings, which show

DETAILED DESCRIPTION

Figure 1:
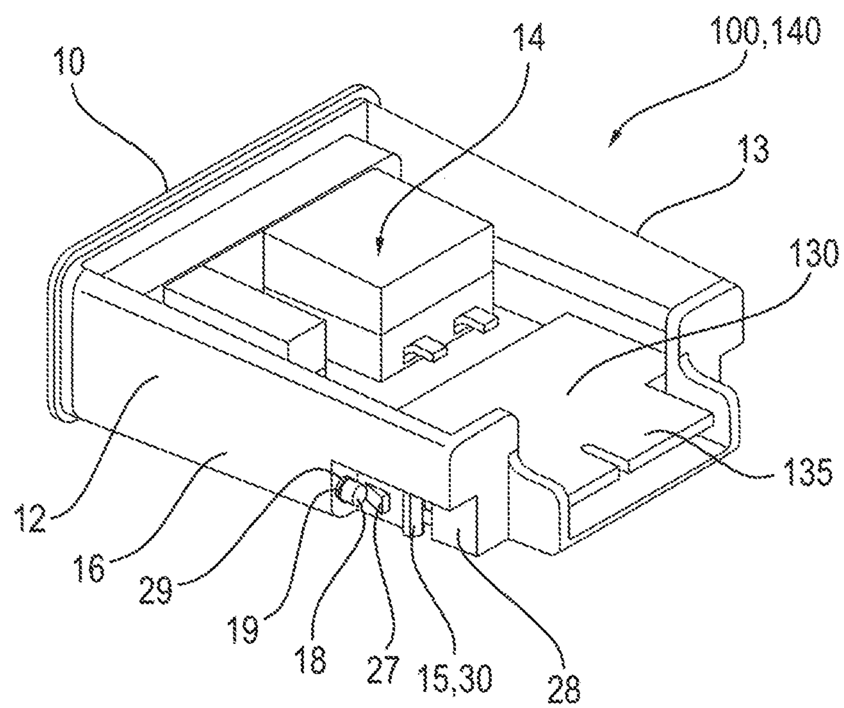
FIG. 1 a perspective rear view of a socket insert according to the invention according to a preferred exemplary embodiment.

FIG. 1 shows the socket insert 100 with a receiving space 14, which is bounded by side walls 12, 13 and a front plate 10. The socket insert 100 forms a support or a housing for one or more sockets 110, 120, which are accessible via plug openings 11 in the front plate 10. The socket insert 100 depicted is preferably a socket insert for an electrosurgical device, in particular an HF surgical device. The socket insert 100 comprises overall three sockets 110, 120, wherein a first socket 110 and two second sockets 120 are provided. The second sockets 120 form a socket pair. In addition, arranged in the receiving space 14 is a printed-circuit board 130 forming a rear plug-and-socket connection 135 such that the sockets 110, 120 of the socket insert 100 can be connected via the plug-and-socket connection 135 of the printed-circuit board 130 to components of an electrosurgical device.

As may be further identified in FIG. 1, the first side wall 12 of the socket insert 100 comprises a guide channel 16 arranged perpendicular to the front plate 10. The side wall 12 is arranged at an acute angle to the front plate 10 so that the width of the socket insert in the area of the front plate is greater than it is in an area arranged at a distance from the front plate. The guide channel 16 comprises a rear outlet opening 29 that opens into a recess 28 in the first side wall 12. A corresponding design comprises the second side wall 13. Insofar, with the exemplary embodiment of the socket insert 100 shown, two side walls 12,13 are provided each of which comprising a guide channel 16. The guide channels 16 each comprise a rear outlet opening 29. In addition, in a backward area of the socket insert 100, the side walls 12, 13 are provided with a recess 28 in each of which a latching means or latching device 15 is arranged. It is clearly identifiable in FIG. 1 that, in the extension of the longitudinal axis of the guide channel, the latching means 15 is substantially in alignment with the guide channel 16.

The latching means 15 comprises a wedge-shaped projection 27 arranged in alignment with the guide channel 16. An outwardly directed latching nose 30 is provided at a distance from the wedge-shaped projection 27. The latching nose 30 is arranged at a free end of the latching means 15. It is also possible for the wedge-shaped projection 27 to pass directly into the latching nose 30 and for there to be no distance between the two (not shown).

With the socket insert 100 depicted, a manipulating rod 18 extends through the guide channel 16. The length of the manipulating rod 18 is greater than the length of the guide channel 16. In particular, a first end of the manipulating rod 18 protrudes over the outlet opening 29. The manipulating rod 18 is preferably in alignment with the wedge-shaped projection 27 of the latching means 15. At its first end, the manipulating rod 18 comprises a stop 19, which interacts with the outlet opening 29 so that an axial movement of the manipulating rod 18 in the direction of the front plate 10 of the socket insert 100 is limited. The stop 19 can, for example, be embodied as an annular rib with a larger diameter than that of the guide channel 16.

Figure 2:
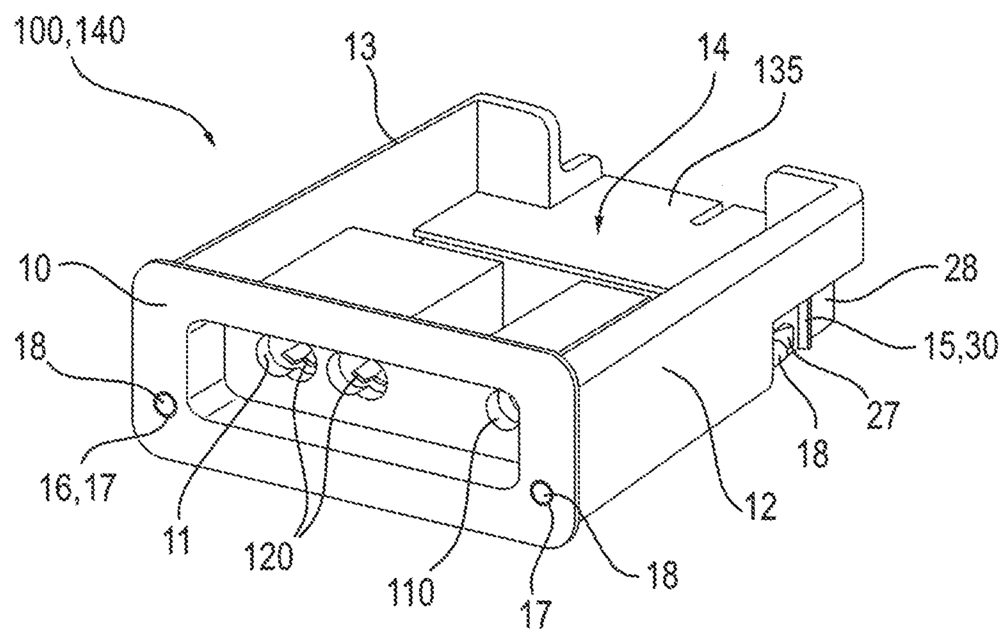
FIG. 2 a perspective front view of the socket insert shown in FIG. 1.

It may be clearly identified in FIG. 2 that the guide channels 16 in the front plate each form an access hole 17. The access hole 17 is closed by the manipulating rod 18. In locked position of the socket insert 100, a second end of the manipulating rod 18 preferably forms a common plane with the front plate 10. In other words, the distance between a front end face of the manipulating rod 18 and the stop 19 corresponds to the length of the guide channel 16.

It may also be identified in FIG. 2 that the front plate 10 comprises a countersunk middle part, in which the plug openings 11 are arranged. The plug openings 11 permit access to the first and second sockets 110, 120.

Figure 3:
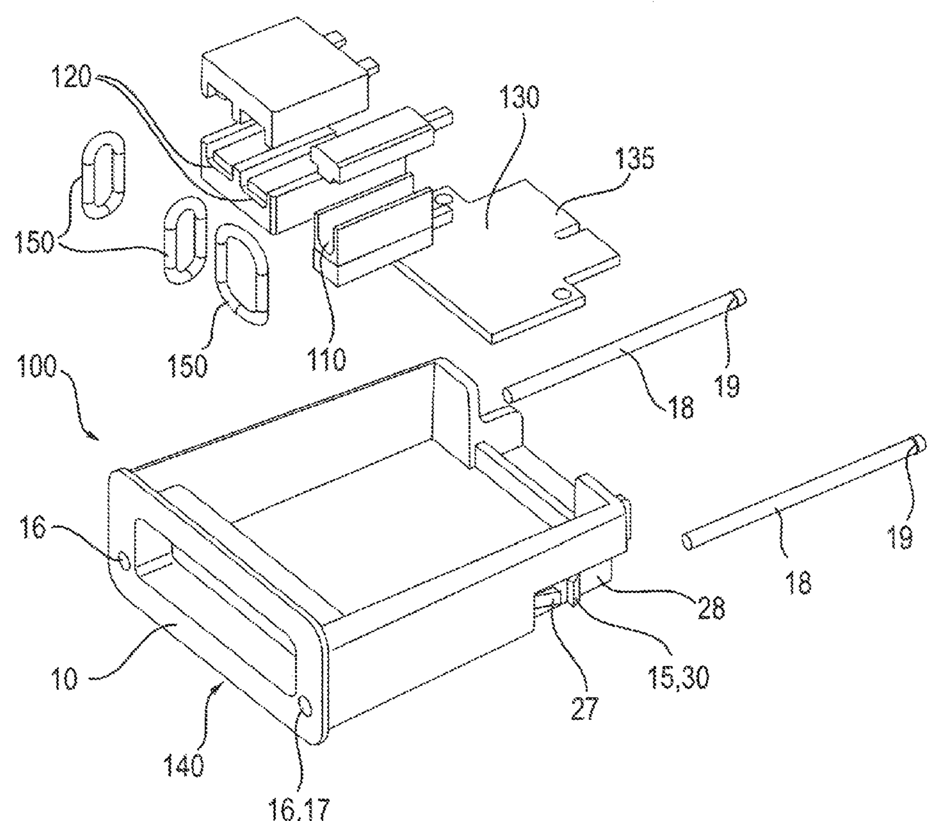
FIG. 3 an exploded view of the socket insert shown in FIG. 1.

In the exploded view shown in FIG. 3, the inner structure of the socket insert 100 can be clearly identified. The socket insert 100 in particular comprises an internal housing 140, which is preferably formed in one piece. The internal housing 140 can be produced as an injection-moulded part. The internal housing 140 comprises the front plate 10 and the side walls 12, 13, which are securely connected to or formed in one piece with the front plate 10. In this way, the internal housing 140 bounds the receiving space 14 for the electronic components, which in particular receives the individual sockets 110, 120 and the printed-circuit board 130. Also identifiable in FIG. 3 are spring means 150, by means of which the plug openings of the individual sockets 110, 120 are embodied variably so that pins with different diameters can be plugged into the sockets 110, 120 with high contact stability.

The guide channels 16 are also formed in one piece with the internal housing 110 or the socket insert 100. The guide channels 16 receive the manipulating rods 18 which interact with the latching means 15 to unlock the socket insert 100. The manipulating rods 18 substantially form tappets, which, due to axial displacement act on the latching means 15 so that the latching nose 30 is directed inward to unlock the socket insert 100. The latching means 15 substantially forms a snap-in hook, which can be brought into unlocked position by manipulating the manipulating rod 18. Here, the manipulating rod 18 is pushed against the wedge-shaped projection 27 so that the rear, first end of the manipulating rod 18 slides along the oblique plane of the wedge-shaped projection 27. This effects an inwardly directed deflection of the latching means 15.

Figure 4:
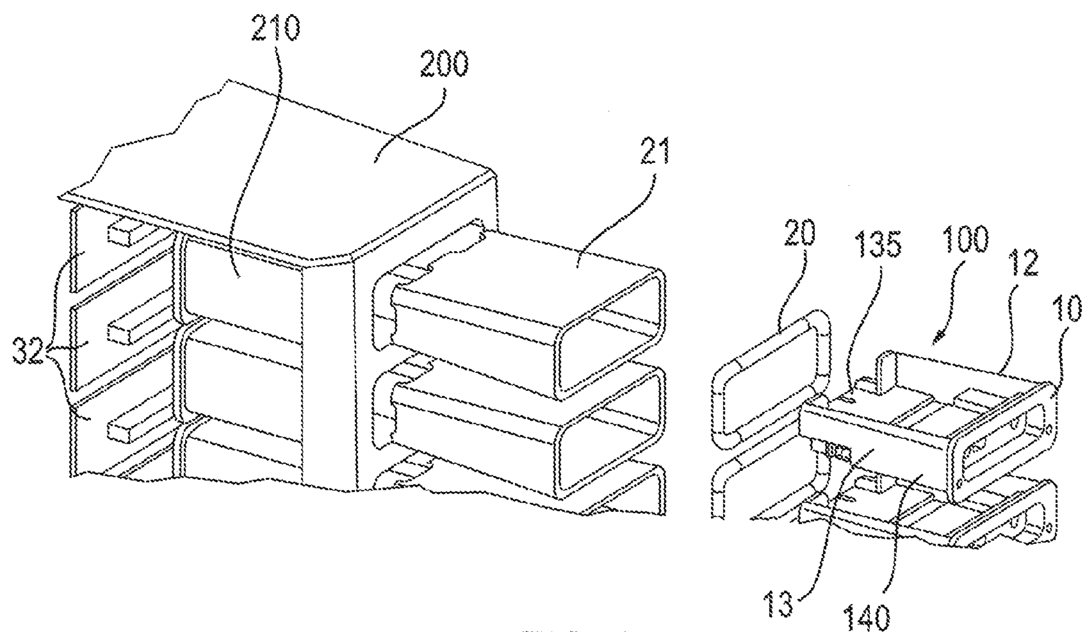
FIG. 4 an exploded view of an area of a device housing of an electrosurgical device with the socket insert shown in FIG. 1.

The socket insert 100 can be connected with a slide-in housing 21, which in turn can be securely arranged in a device housing 200 of an electrosurgical device (FIG. 4). The slide-in housing 21 preferably completely encloses the receiving space 14 so that the electronic components arranged therein are protected against access. The slide-in housing 21 can be made of a transparent plastic, for example by injection moulding. Generally, the slide-in housing 21 preferably forms a light guide, which can be optically coupled to a translucent frame 20, which, in assembled condition of the socket insert 100, frames the front plate 10.

Figure 5:
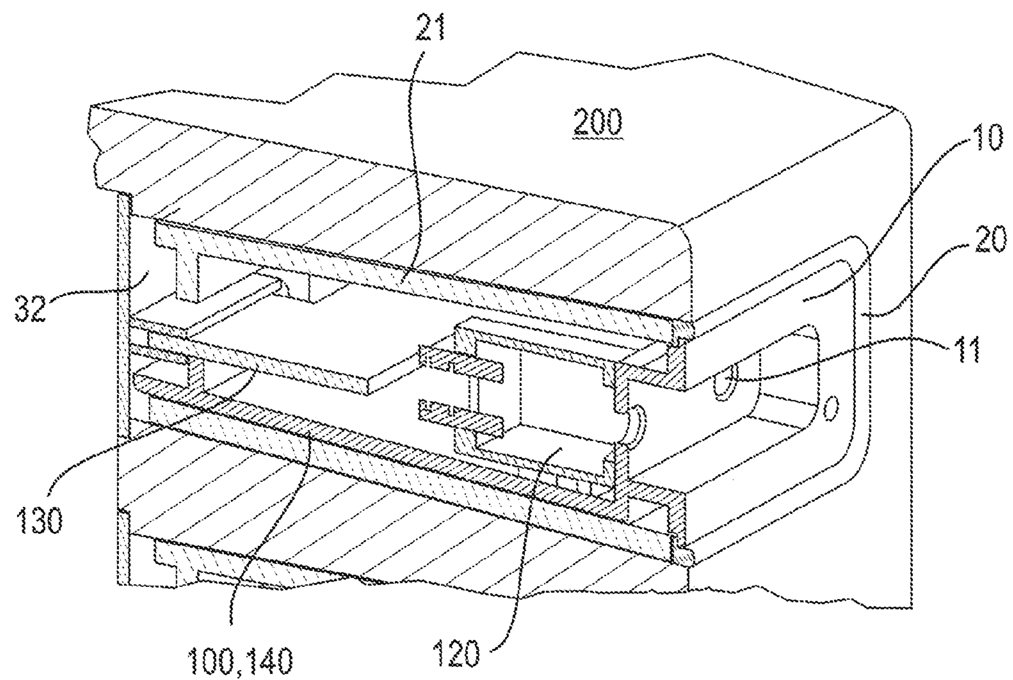
FIG. 5 a perspective sectional view of the device housing shown in FIG. 4 with an inserted socket insert.
Figure 6:
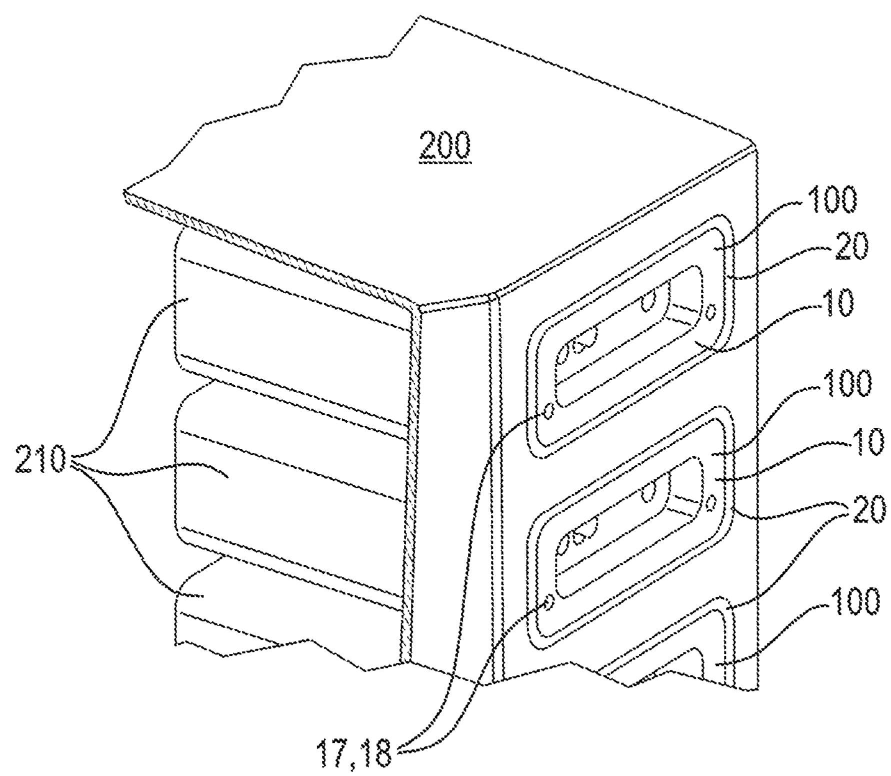
FIG. 6 a further perspective sectional view of the device housing shown in FIG. 4.
Figure 7:
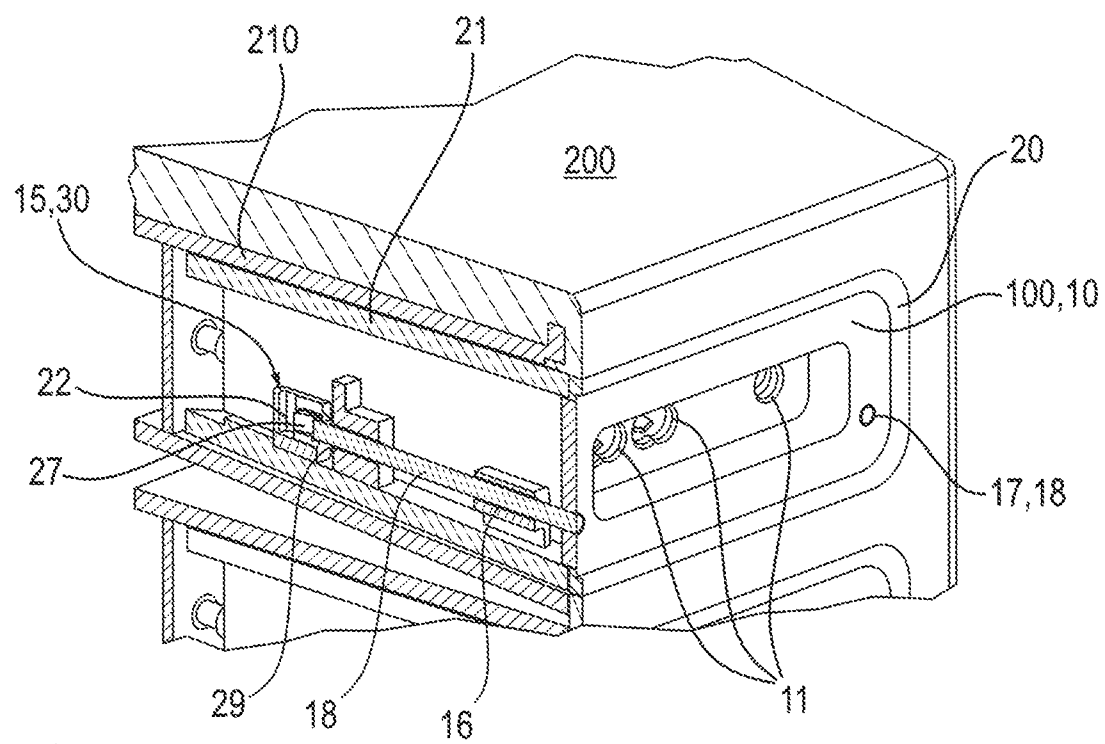
FIG. 7 a sectional view through the device housing shown in FIG. 4 and the socket insert used therein.

The slide-in housing 21 is preferably dimensioned such that, in built-in condition of the socket insert 100, the front plate 10 is in alignment with a housing front of the electrosurgical device. The translucent frame 20 can protrude over the front plate 10 or the housing front. This enables a three-dimensional light effect, which is aesthetically appealing. The frame 20 protruding over the front plate 10 is clearly identifiable in FIG. 5.

The translucent frame 20 can be used as an operating mode display, wherein light from a light source is coupled into the translucent frame 20 via the slide-in housing 21 embodied as a light guide. The light source is preferably formed from a backlighting printed circuit board 32 arranged behind the socket insert 100 in the device housing 200. FIG. 4 shows a plurality of backlighting printed circuit boards 32 each comprising a plurality of light-emitting diodes. The light-emitting diodes serve as light sources for the slide-in housing 21 embodied as a light guide.

As may be clearly identified in FIGS. 4-8, the device housing 200 comprises one or more socket holders 210, which are dimensioned such that they receive the socket insert 100, in particular the slide-in housing 21. The slide-in housing 21 can be securely locked in the socket holder 210. The slide-in housing 21 preferably remains permanently in the socket holder 210. The socket insert 100, on the other hand, is latched detachably in the slide-in housing 21. The latching mechanism ensures a positive connection between the socket insert 100 and the slide-in housing 21. A removal tool 23 can be used to unlock the socket insert 100 and pull it out of the slide-in housing 21.

Figure 8:
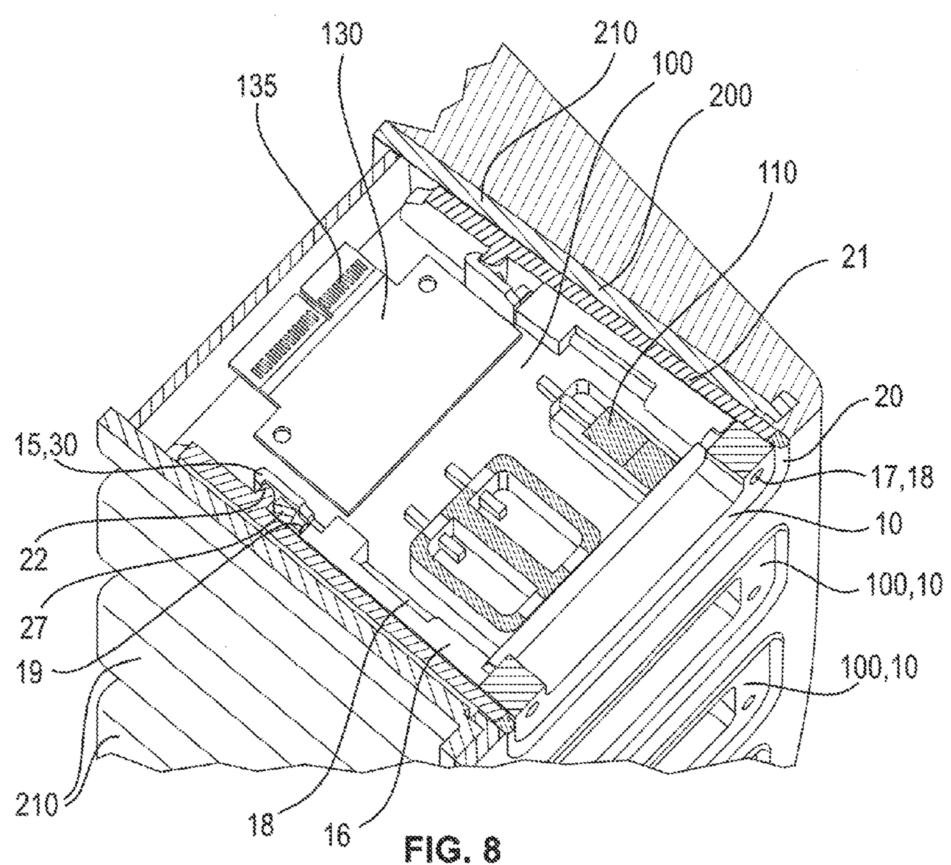
FIG. 8 a horizontal sectional view through the device housing shown in FIG. 4 and the socket insert.

The latching means 15 for the connection of the socket insert 100 to the slide-in housing 21 can be clearly seen in FIG. 8. It is in particular identifiable in FIG. 8 that the latching means 15 of the socket insert 100 comprises a wedge-shaped projection 27 and a latching nose 30. In locked position, the latching nose 30 grips a complementary means 22 of the slide-in housing 21 from behind so that a positive connection is established between the socket insert 100 and the slide-in housing 21. The complementary means 22 is formed from an inwardly projecting latching projection formed in one piece with the slide-in housing 21.

Figure 9:
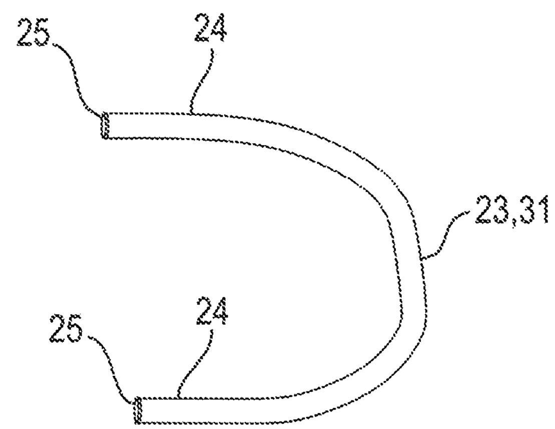
FIG. 9 a perspective view of a removal tool for the socket insert according to the invention according to a preferred exemplary embodiment.

A removal tool 23 shown in FIG. 9 is used to unlock the socket insert 100. The removal tool 23 comprises two unlocking rods 24 connected to each other by a clip 31. The clip 31 and the unlocking rods 24 are preferably formed in one piece with each other. The unlocking rods 24 each comprise a free end, which is provided with a protruding edge 25. The protruding edge 25 substantially forms an annular projection at the free end of the unlocking rod 24. The diameter of the protruding edge 25 is preferably smaller than the diameter of the guide channel 16 so that the removal tool 23, in particular the unlocking rod 24, can be easily introduced into the guide channel 16. In particular, the removal tool 23 can be introduced into the guide channels 16 via the access openings 17 and hence comes into contact with the manipulating rod 18 arranged in the guide channel 16. The removal tool 24 can also displace the manipulating rods 18 axially in the guide channel 16. Here, in each case the rear, first end of the manipulating rod 18 comes into contact with the wedge-shaped projection 27 of the latching means 15. Therefore, the introduction of the removal tool 23 deflects the latching means 15 and transfers it from locked position into unlocked position.

Figure 10:
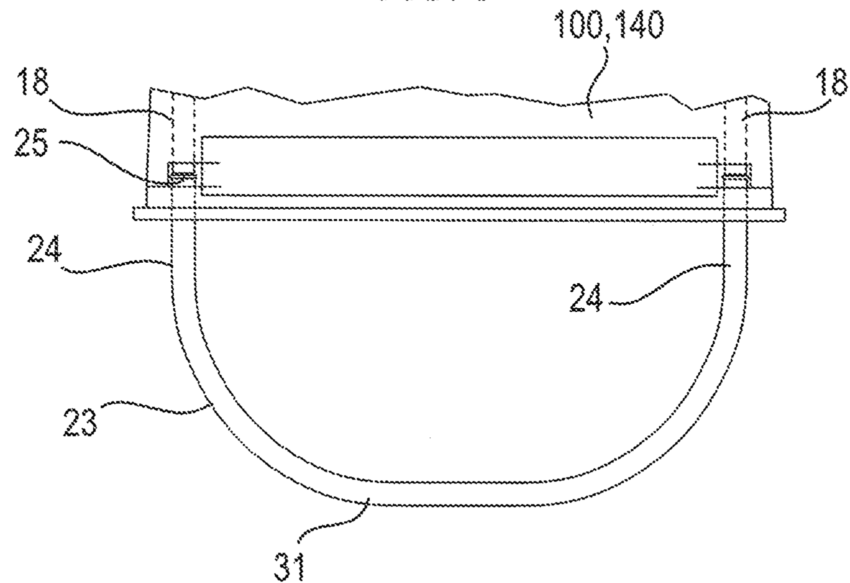
FIG. 10 a top view of the removal tool shown in FIG. 9 connected to the socket insert.
Figure 11:
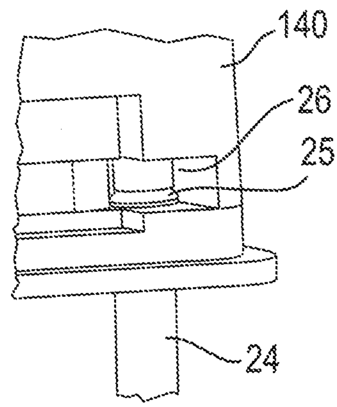
FIG. 11 a detailed view of the connection between the removal tool and the socket insert shown in FIG. 10.

As can be identified in FIGS. 10 and 11, each guide channel 16 preferably comprises a recess 26 embodied close to the front plate 10 in the side wall 12, 13. The recess 26 is embodied such that the protruding edge 25 of the removal tool 23 can establish a positive connection with the socket insert 100. This enables the removal tool 23 to be used as a retaining clip in order to remove the socket insert 100 from the device housing 200.

To install the socket insert 100, it is simply pushed into the slide-in housing 21, which is securely arranged in the socket holder 210 of the device housing 200, in particular cohesively or mechanically anchored. For example, the slide-in housing 21 can be in a cohesive or positive connection with the socket holder 210. Pushing the socket insert 100 causes the latching means 15 to latch with the complementary means 22 in the slide-in housing 21 so that the socket insert 100 is fixed in the device housing 200.

Since the slide-in housing 21 simultaneously forms a light guide, the latching mechanism or snap-in hook mechanism of the socket insert 100 is arranged in the recesses 28 of the side walls 12, 13. This prevents the latching mechanism from impeding a light path in the light guide. The electrical connection between the sockets 110, 120 and the electrical components in the electrosurgical device is established via the printed-circuit board 130 comprising a rear plug-and-socket connection 135. The electrical connection is provided by pushing the socket insert 100 into the socket holder 210, wherein the plug connection 135 engages with a corresponding socket connection in the device housing 200.

The removal tool 23 acting on the manipulating rods 18 or tappet arranged in the guide canals 16 is used to change the socket insert 100. Via the manipulating rods 18, the removal tool can deflect the latching nose 30 of the latching means 15 inward so that the socket insert 100 is released. Pushing the removal tool 23 into the guide channels 16 causes the removal tool 23 to establish a positive connection with the socket insert 100. To this end, the recess 26 is provided in the guide channels 16 into which the protruding edge 25 of the unlocking rod 24 engages. The recess 26 can be arranged at a distance of approximately 3 mm to 4 mm from the front plate 10 in the guide channel 16. To establish the positive connection between the removal tool 23 and the socket insert 100, the removal tool 23 is tilted. This causes the protruding edge 25 to engage positively with the recess 26. The removal tool 23 can then be used to pull the socket insert 100 out of the slide-in housing 21.

Alternatively, it is possible, instead of the manipulating rod 18, to use a removal tool 23 whose unlocking rods 24 have a sufficient length to act directly on the latching means 15. However, it is advantageous to use manipulating rods 18, which are securely integrated in the guide channels 16 since in this way the socket insert 100 is completely closed. The manipulating rods 18, which in locked position are flush with the front plate 10, provide the socket insert 100 with an aesthetically appealing overall impression.

When the manipulating rod 18 is pushed forward, the stop 19 of the manipulating rod 18 also latches with the wedge-shaped projection 27 so that the manipulating rod 18 is locked in the unlocked position. Insofar, the stop 19 has a dual function. On the one hand, the stop 19 makes it impossible for the manipulating rod 18 to be removed forwardly, i.e. via the access hole 17, out of the guide channel 16 in locked condition. At the same time, in unlocked position, the stop 19 prevents the manipulating rod 18 falling back into locked position. In this way, the possibility of a socket insert 100 that has already been removed from holder 110 being reused in the socket holder 210 can be prevented. This is only possible if the manipulating rod 18 has been returned manually to its original position that is the locked position.

With the present invention, the socket insert 100 can be replaced without having to open the device housing 200 of the electrosurgical device. In this way, access to current-carrying components of the electrosurgical device during the replacement of the socket insert 100 is avoided. Therefore, no additional safety check is necessary following the replacement of the socket insert 100. This reduces the amount of maintenance for electrosurgical devices. It also simplifies the replacement of the socket insert 100 since no expensive tools have to be used to this end. In particular, no screwed connections or the like have to be loosened in order to replace the socket insert 100. Instead, the socket insert 100 is replaced simply and quickly using the removal tool 23.

LIST OF REFERENCE NUMBERS

100 Socket insert
110 First socket
120 Second socket
130 Printed-circuit board
135 Plug-and-socket connection
140 Internal housing
150 Spring means
200 Device housing
210 Socket holder
10 Front plate
11 Plug opening
12 First side wall
13 Second side wall
14 Receiving space
15 Latching means
16 Guide channel
17 Access hole
18 Manipulating rod
19 Stop
20 Translucent frame
21 Slide-in housing
22 Complementary means
23 Removal tool
24 Unlocking rod
25 Protruding edge
26 Recess
27 Wedge-shaped projection
28 Recess
29 Outlet opening
30 Latching nose
31 Clip
32 Backlighting printed circuit board

What is claimed is:

1. An apparatus comprising a socket insert for an electrosurgical device, wherein the socket insert comprises:
- a front plate, comprising at least one plug opening,
- first and second side walls, which are connected to the front plate and bound a receiving space for electronic components and
- at least one latching device, which is connected to the first side wall and can be transferred from a locked position into an unlocked position, wherein at least the first side wall comprises a guide channel, which forms an access hole in the front plate and through which the latching device can be manipulated for unlocking.

2. The apparatus according to claim 1, wherein an axially displaceable manipulating rod is arranged in the guide channel, wherein a first end of the manipulating rod is embodied to unlock the latching device and can be moved out of the guide channel.

3. The apparatus according to claim 2, wherein the manipulating rod's length is greater than the guide channel's length.

4. The apparatus according to claim 2, wherein the manipulating rod comprises a stop, which is configured to interact with the guide channel for limiting the axial movement of the manipulating rod.

5. The apparatus according to claim 2, wherein the latching device comprises a wedge-shaped projection, which is in alignment with the manipulating rod, wherein the wedge-shaped projection's height increases in direction of advance of the manipulating rod.

6. The apparatus according to claim 4, wherein the latching device comprises a wedge-shaped projection, which is in alignment with the manipulating rod, wherein the wedge-shaped projection's height increases in direction of advance of the manipulating rod.

7. The apparatus according to claim 1, wherein the latching device comprises an outwardly directed latching nose, which can be moved inward toward the receiving space for the unlocking.

8. The apparatus according to claim 6, wherein the latching device comprises an outwardly directed latching nose, which can be moved inward toward the receiving space for the unlocking.

9. The apparatus according to claim 1, wherein the first and second side wall each comprise a guide channel.

10. The apparatus according to claim 1, wherein the front plate comprises a translucent frame, which is connected to a light guide.

11. The apparatus according to claim 10, wherein the light guide forms a slide-in housing, which completely surrounds the receiving space and can be connected to a light source.

12. The apparatus according to claim 11, wherein the slide-in housing comprises at least one complementary connection portion configure to connect with the latching device of the side wall, wherein the complementary connection portion is arranged on an inner wall of the slide-in housing outside the light path.

13. The apparatus of claim 1 further comprising an electrosurgical device with at least one of the socket insert.

14. The apparatus according to claim 1 further comprising a removal tool comprising at least one unlocking rod with a free end, which can be introduced into the guide channel.

15. The apparatus according to claim 14, wherein the unlocking rod comprises a protruding edge at the free end, wherein the protruding edge's diameter is smaller than the guide channel's diameter.

16. The apparatus according to claim 15, wherein the guide channel comprises a recess, which can be gripped from behind by the protruding edge of the removal tool for the removal of the socket insert from the electrosurgical device.

* * * * *